United States Patent [19]
Madison

[11] Patent Number: 4,569,989
[45] Date of Patent: Feb. 11, 1986

[54] METHOD OF INHIBITING MICROBIAL ACTIVITY WITH CERTAIN BIOACTIVE SULFONE POLYMERS

[75] Inventor: Norman L. Madison, Midland, Mich.

[73] Assignee: The Dow Chemical Company, Midland, Mich.

[21] Appl. No.: 685,516

[22] Filed: Dec. 24, 1984

[51] Int. Cl.$^4$ .............................................. C08G 75/22
[52] U.S. Cl. .................................. 528/386; 106/18.34; 252/180; 424/78; 523/122; 525/906
[58] Field of Search ........................ 528/386; 523/122; 106/18.34; 525/906; 424/78; 252/180

[56] References Cited
U.S. PATENT DOCUMENTS 2,293,023  8/1942  Hills et al. ............................ 528/386
4,179,757  12/1979 Crawford et al. ............... 528/386 X Primary Examiner—Theodore E. Pertilla

[57] ABSTRACT

A method of inhibiting microbial growth by employing an addition copolymer is disclosed. The addition copolymer consists essentially of an olefin and sulfur dioxide; said olefin containing at least one substituent selected from the group consisting of hydrogen, chloride, and fluoride radicals. These compositions inhibit bacterial growth while functioning as plastic materials and can be used in coatings, packaging, paints, structural members and supports.

3 Claims, No Drawings

METHOD OF INHIBITING MICROBIAL ACTIVITY WITH CERTAIN BIOACTIVE SULFONE POLYMERS

BACKGROUND OF THE INVENTION

This invention relates to compositions which inhibit microbial growth. The composition consists essentially of an addition copolymer formed by reacting an olefin with sulfur dioxide.

Though the polymer is well known in the art, its use as a biocide is not. The copolymer of the present invention will inhibit microbial activity to provide sterile surfaces. It will actually kill activity on the treated surface.

The addition copolymer of the present invention consists essentially of sulfur dioxide and a monomeric olefin. This copolymer is disclosed in U.S. Pat. No. 3,820,963, but the disclosed use is for modified turbine engine fuels. U.S. Pat. No. 3,396,115 also discloses the polysulfone resin of the present invention, but for use as dry cleaning detergents. The copolymer is further disclosed in U.S. Pat. No. 3,657,200 for use as permanent sizing agents for fabrics.

The biocompatibility of the copolymers of the present invention is disclosed in U.S. Pat. Nos. 3,928,294 and 4,179,757. However, these patents do not disclose the biocidal activity of the copolymers, which is the novelty of the present invention.

Though sulfur dioxide is a known biocide, the copolymer of the present invention is not. U.S. Pat. Nos. 3,272,784 and 3,272,782 disclose copolymers of sulfur dioxide with comonomers derived from the reaction of ar-vinylidene $\alpha$-haloalkyl aromatic compounds with nucleophilic reagents for use as slime-control agents. Other known sulfur-containing biocides include 1,2-dichloro-cyano-vinyl sulfides as disclosed in U.S. Pat. No. 4,238,405; aqueous liquid emulsions of bistrichloromethyl sulphone as disclosed in U.S. Pat. No. 3,996,155; 2,5-dihalophenyl-$\beta$-substituted sulfone compounds as disclosed in U.S. Pat. No. 4,206,235; arylthio sulfphone derivatives as described in U.S. Pat. No. 4,335,142; 7-(nitrogen-containing heterocyclic carbonamido) cephalosporanic acid as described in U.S. Pat. No. 3,308,120; and organic sulphones containing nitrile or carbonamide groups as described in U.S. Pat. No. 4,079,148. The advantage of the copolymers of the present invention versus the known bioactive plastic products is that they do not appear to involve a leachable species.

Silicones have also been disclosed as biocides. U.S. Pat. Nos. 3,817,739 and 3,865,728 disclose polysiloxane resins which inhibit the growth of algae on any solid, while U.S. Pat. No. 3,794,736 discloses organosilicon-substituted amines which inhibit the growth of bacteria and fungi.

Di(vinyl)alkyl polysulfides were disclosed in U.S. Pat. No. 4,438,259 as being resistant to, but not inhibiting, fungal attack.

SUMMARY OF THE INVENTION

It has been discovered in accordance with this invention that addition copolymers consisting essentially of a monomeric olefin and sulfur dioxide inhibit microbial growth as well as function as plastic materials such as wraps, packages, paints, coatings, structural members, and supports.

Thus, the invention is a method of inhibiting microbial growth by employing an addition copolymer consisting essentially of at least one mole of a monomeric olefin for each mole of sulfur dioxide; said olefin containing at least one substituent selected from the group consisting of hydrogen, chloride, and fluoride radicals.

DETAILED DESCRIPTION OF THE INVENTION

Any addition copolymer consisting essentially of at least one mole of a monomeric olefin for each mole of sulfur dioxide, said olefin containing at least one substituent selected from the group consisting of hydrogen, chloride, and fluoride radicals, can be employed for the purposes of this invention.

The addition copolymer of the present invention can be prepared by techniques well known to those skilled in the art. They can be prepared in the presence of any suitable catalyst such as a free radical source, light, peroxide, or azo nitrile. However, they are preferably prepared by solution polymerization or by suspension polymerization of the olefins with sulfur dioxide.

The solution polymerization employs specific chlorinated solvents such as chloroform, methyl chloroform, methylene chloride, mixtures thereof, or mixtures of the above with carbon tetrachloride with a minimum amount of catalyst to insure the preparation of high molecular species as is known in the art. Other solvents such as benzene and liquid sulfur dioxide can be used, however, the reaction time and rate of conversion is longer. The suspension polymerization technique uses suspending agents such as nonionic surfactants, anionic surfactants, and copolymers of alkyl styrenes with N-vinyl heterocyclic monomers.

It is preferred that the monomeric olefin employed in the copolymer of the present invention contains the unit with the general structure:

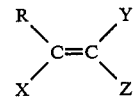

wherein R is selected from the group consisting of hydrogen, chloride, and fluoride radicals; while X, Y and Z can be any radical. Examples of suitable radicals for X, Y and Z include hydrogen, halogens, alkyls, cycloalkyls, aryls, arylalkyls, nitriles, and carboxyalkyls, to name a few. Specific examples of suitable radicals for X, Y, and Z include chlorides, methyls, phenyls, and benzyls. It is not important for the purposes of this invention that the radicals X, Y and Z be the same. The olefin employed in the addition copolymer of the present invention can also be mixtures of the monomeric olefins just described.

Though there is no real limit on the number of carbon atoms comprising the monomeric olefin, it is preferred that it contain between 2 and 40 carbon atoms. It is further preferred that the olefin be an alpha for ease of polymerization.

Useful alpha olefins are normal (linear) alpha monoolefins such as butene-1, hexene-1, octene-1, decene-1, dodecene-1, tetradecene-1, and the like.

Branched chain monomers are also useful to prepare the olefin polysulfones used in this invention. Examples of such monomers include 3-methyl butene-1; 2,3-dimethyl butene-1; 2,4,4-trimethyl pentene-1; 6,6- dimethyl octene-1; 4,6-dimethyl heptene-1; 2-propylpentene-1; 3-ethyl-2-heptene; 3,3,5,5-tetramethyl hexene-1; 6,6-diethyleicosene-1; 4,4-dimethyl octadiene-1; 3,3,5,5-tetraethyl hexene-1; 3,4-diisopropyl hexene-1; 3,5-di-t-butyl hexene-1; and the like.

If desired, selected crosslinking compounds can also be blended with the alpha olefins. Examples of such crosslinking agents include 1,7-octadiene; 1,3-butadiene; divinyl benzene; diallylcarbonate; diallyl phthalate; 1,3-cyclohexadiene; 4-methyl-1,3-pentadiene; 1,5-cyclooctadiene; 1,5,9-cyclododecatriene; 2-methyl-2,4-hexadiene; 1,11-dodecadiene; diallyl glycerol ether; diallyl phosphate; dicyclopentadiene; allyl acrylate; ethylene glycol dimethacrylate; triallyl amine; vinyl-4-allyl benzoate; diallyl ether of polypropylene glycol; and the like.

Though the polysulfones which are useful in this invention are of substantially linear molecular structure, alpha mono-olefins commercially available from cracked waxes may be employed. These contain olefins of various chain lengths both normal and branched chain α-olefins with a small amount of diolefins.

It is preferred, however, that butylene be employed as the olefin for the purposes of this invention.

The olefins of the present invention can be prepared by techniques well known to those skilled in the art. The telomers are available from the Ziegler polymerization of ethylene.

The biocides of the present invention can be employed as outdoor paints for warm, high humidity climates; post harvest crop treatment such as emulsion dipping of skinned fruits and vegetables to minimize rotting; tarps, wraps, bins, trays, coverings, etc., to minimize pest infestation of skinned fruits and vegetables; coatings for hospital surgical packs to maintain post irradiation sterility; bandages or bandage coatings to prevent infection; paints for hospital rooms, furnishings, and appurtenances to minimize sanitizer and scrubber usage and to compliment sanitizer and scrubber use; powders, dusts, liquids, or gels to inhibit or control athletes feet; powders, dusts, liquids, or gels to be used topically to prevent, inhibit, treat or control microbial infestation or infection; powders, liquids, gels, or films to impart bioactive properties to other materials by blending, coating or laminating; decorative as well as functional utility to prevent discoloration caused by microbial infestation, especially mildew staining; trough liners or interior pipe coatings to maintain good flow of water in systems where clinging wall growth would have detrimental effects; pool, pond, or storage tank liners or coatings to inhibit surface organic growth; awnings, curtains, and shades where mildew growth is undesirable; and can liners to inhibit microbial growth in paints. Other applications include those where it is desirable to inhibit the growth of algae, fungus, molds, yeasts, rusts mildew, barnacles, and bacteria. Specifically, the copolymers are active against fungi such as *Penicillium glaucum, Chaetomium globosum,* and *Rhizopus nigricans;* bacteria such as *Bacterium coli, Bacterium pyocyaneum,* and *Aerobacteraerogenes;* slimes such as slime-forming organisms which utilize caprolactam; green algae such as *Stichococcus bacillaris Naegeli, Euglena gracilis Klebs,* and *Chorella pyrenoidosa Chick;* blue algae such as *Phormidium foredarum Gromont* and *Oscillatoria geminata Meneghini;* silacaceous algae such as *Phaedodactylum tricornutum Bohlin.*

The apparent non-leaching activity of these polymers may permit using them to replace toxic leachable biocides which can contaminate water systems. In addition, since these polymers are not soluble in water, they should retain their activity at a near constant level for extended periods.

The copolymers can be applied together with inert solids to form dusts, or can be suspended in a suitable liquid diluent, preferably water. In place of water there can be employed organic solvents as carriers such as hydrocarbons, ketones, chlorinated hydrocarbons, esters. Examples of suitable hydrocarbons include benzene, toluene, xylene, kerosene, diesel oil, fuel oil, and petroleum naptha. Examples of suitable ketones include acetone, methyl ethyl ketone, and cyclohexane. Examples of suitable chlorinated hydrocarbons include carbon tetrachloride, chloroform, trichloroethylene, and perchloroethylene. Examples of suitable esters include ethyl acetate, amyl acetate, butyl acetate, glycol ethers such as monomethyl ether of ethylene glycol and monomethyl ether of diethylene glycol, and alcohols such as ethanol, isopropanol, and amyl alcohols.

There can also be added surface active agents or wetting agents and/or inert solids in the liquid formulations. Examples of suitable surfactants include alkyl sulfonates, alkylaryl sulfonates, alkyl sulfates, alkylamide sulfonates, alkylaryl polyether alcohols, and fatty acid esters of polyhydric alcohols.

The copolymer can also be applied via an aerosol system or as a plasticizer so long as a coherent film is formed. The copolymer can also be molded into the desired shape or object.

Now in order that those skilled in the art may better understand how the present invention can be practiced, the following examples are given by way of illustration and not by way of limitation.

EXAMPLE 1

To prepare the butene sulfur dioxide polymers, the following procedure was used. Azobisisobutyronitrile (0.0138 grams (g)) was added to a glass ampule which was then evacuated and cooled with liquid nitrogen. Butene-1 (0.5 g) and sulfur dioxide (15 g) was added by condensation. The ampule was sealed and then heated to 55° C. for 72 hours. The ampule was again cooled with liquid nitrogen and opened. The glassy polymer was dissolved in an excess of methylene chloride, precipitated with hexane and dried. An IR spectrum of the product identified it as a 1/1 copolymer of the two comonomers.

A one-inch square coupon was prepared by compression molding the polymer made above. The coupon (⅛ inch thick) was cleaned with swabs which had been dipped in 70 percent aqueous ethanol. The coupon was placed in a 37° C. incubator overnight in an individual petri dish. After drying the coupon was inoculated with 20 milliliters (ml) of a 24 hour old culture of the bacteria, *Esherichia coli.* Organisms were recovered at zero time with 10 ml of 0.85 percent aqueous solutions of sodium chloride. Appropriate dilutions and plate counts were made to determine that $6.8 \times 10^7$ organisms were applied to each square coupon. Forty eight hours after treatment the recoverable bacteria population on the coupon had decreased by greater than 99.999 percent. The viable count on a polystyrene control coupon had decreased only by 90 percent, after 48 hours. Most of the population decrease on the control is attributed to dehydration.

EXAMPLE 2

A terpolymer prepared as in Example 1, where 25 percent of the butene-1 is replaced with acrylonitrile, was evaluated as in Example 1. The viable count of the bacteria, *Esherichia coli* dropped by 99.8 percent in 24 hours. The count on the polystyrene control coupon remained the same.

EXAMPLE 3

A 50/50 mixture of butene-1 and butene-2 was used to make a polymer with $SO_2$ as in Example 1. The test results were essentially the same as those of Example 1, i.e., greater than 99.999 percent viable bacteria count decrease after 48 hours.

EXAMPLE 4

The polymer from Example 1 was examined for its ability to inhibit growth of the fungus, *Piricularia grisea*. A cleansed coupon prepared with polymer from Example 1 was placed in a petri dish which contained a culture of wet agar inoculated with *Piricularia grisea*. Only the underside of the coupon was exposed to the culture medium. The dish was covered and allowed to stand for two weeks at room temperature. A control coupon of polystyrene was treated in the same manner. The test coupon showed no visible fungal growth on the underside, whereas extensive growth occurred on the polystyrene control.

With the butene-sulfur dioxide polymer coupon, there was also no zone of inhibition in the culture medium indicating that the inhibition to mold growth did not take place from a leachable species but on the solid polymer surface.

A test to confirm the fungal growth inhibiting ability of these polymers was performed as follows. A coupon of the test polymer of Example 1 and a control of polystyrene were inoculated with *Piricularia grisea* and placed in a humid bell chamber. No growth occurred on either sample indicating that neither polymer supports the growth of this fungus. When a nutrient broth was added to each coupon, extensive fungus growth occurred on the polystyrene control but no visible growth was apparent after two weeks on the test sample. Thus, the butene-sulfurdioxide polymer appears to inhibit the growth of the fungus as well as not supporting growth.

What is claimed is:

1. In a method of inhibiting microbial growth in a system by incorporating a biocide, the improvement of employing as the biocide an addition copolymer consisting essentially of at least one mole of a monomeric olefin for each mole of sulfur dioxide; said olefin containing at least one substituent selected from the group consisting of hydrogen, chloride, and fluoride radicals.

2. The method as defined in claim 1 wherein the addition copolymer consists essentially of 1-2 moles of an α-olefin per mole of sulfur dioxide.

3. The method as defined in claim 2 wherein the olefin is butene.

* * * * *